United States Patent [19]

Shutske et al.

[11] Patent Number: 4,631,286
[45] Date of Patent: Dec. 23, 1986

[54] 9-AMINO-1,2,3,4-TETRAHYDROACRIDIN-1-OL AND RELATED COMPOUNDS

[75] Inventors: Gregory M. Shutske; Frank A. Pierrat, both of Somerset, N.J.

[73] Assignee: Hoechst-Roussel Pharmaceuticals Inc., Somerville, N.J.

[21] Appl. No.: 664,731

[22] Filed: Oct. 25, 1984

[51] Int. Cl.[4] .................. A61K 31/47; C07D 219/10
[52] U.S. Cl. ................................ 514/297; 514/786; 514/787; 546/105; 558/414; 558/423; 558/425; 558/411
[58] Field of Search ............... 546/105; 514/297, 786, 514/787

[56] References Cited

U.S. PATENT DOCUMENTS

| | | | |
|---|---|---|---|
| 3,033,866 | 5/1962 | Saggiomo et al. | 546/102 |
| 3,122,553 | 2/1964 | Seneca | 546/105 |
| 3,232,945 | 2/1966 | Sigal, Jr. et al. | 546/105 |
| 4,284,627 | 8/1981 | Raether et al. | 514/297 X |

OTHER PUBLICATIONS

Magidson, et al., Chemical Abstracts, vol. 31, 5800[7] (1937).
Sargent, et al., J. Org. Chem., vol. 11, pp. 350-362 (1946).
Sargent, et al., J. Org. Chem., vol. 12, pp. 567-570 (1947).
Sargent, et al., J. Org. Chem., vol. 12, pp. 571-576 (1947).
Stephen, et al., J. Chem. Soc. (1947), pp. 1034-1039.
Desai, et al., J. Indian Chem. Soc., vol. 37, No. 9, pp. 553-556 (1960).
Steinberg, et al., J. Med. Chem., vol. 18, No. 11, pp. 1056-1061 (1975).
Brian, et al., Chemical Abstracts, vol. 62, 6459e (1965).
Albert, The Acridines, 2nd ed., St Martins Press, N.Y. (1966), pp. 431-432.
Patnaik, et al., J. Med. Chem., vol. 9, pp. 483-488 (1966).
Konshin, et al., Chemical Abstracts, vol. 76, 34080k (1972).
Konshin, et al., ('T'), Chemical Abstracts, vol. 81, 120411d (1974).
Koupilova, et al., Chemical Abstracts, vol. 96, 155388p (1982).
Davies, Drug Development Research, vol. 5, pp. 69-76 (1985).
Johns, et al., Drug Development Research, vol. 5, pp. 77-96 (1985).
Ellman, et al., Biochemical Pharmacology, vol. 7, pp. 88-95 (1961).
Schindler, et al., Drug Development Research, vol. 4, pp. 567-576 (1984).
Bartus, et al., Science, vol. 209, pp. 301-303 (07/11/80).
Broekkamp, et al., Psychopharmacology, vol. 83, pp. 122-125 (1984).
Komiskey, et al., Psychopharmacology, vol. 73, pp. 304-305 (1981).

Primary Examiner—Donald G. Daus
Assistant Examiner—Diana G. Rivers
Attorney, Agent, or Firm—Tatsuya Ikeda

[57] ABSTRACT

There are disclosed compounds having the formula

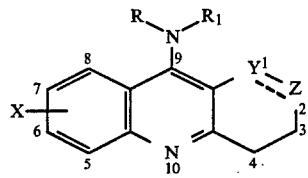

wherein X is hydrogen, loweralkyl, loweralkoxy, halogen, hydroxy, nitro, NHCOR$_2$ wherein R$_2$ is loweralkyl, or a group of the formula NR$_3$R$_4$ wherein R$_3$ and R$_4$ are independently hydrogen or loweralkyl; R and R$_1$ are independently hydrogen, loweralkyl, phenylloweralkyl, phenylloweralkyl in which the phenyl group is substituted by one or more loweralkyl, loweralkoxy, halogen, hydroxy or trifluoromethyl, diphenylloweralkyl or diphenylloweralkyl in which one or both phenyl groups are substituted by one or more loweralkyl, loweralkoxy, halogen, hydroxy or trifluoromethyl; Y is C=O or CR$_5$OH wherein R$_5$ is hydrogen or loweralkyl; Z is CH$_2$ or C=CR$_6$R$_7$ wherein R$_6$ and R$_7$ are independently hydrogen or loweralkyl; or Y and Z taken together is CR$_5$=CH wherein CR$_5$ and CH correspond to Y and Z respectively; an optical antipode thereof, or a pharmaceutically acceptable acid addition salt thereof, which are useful for enhancing memory, methods for synthesizing them, and pharmaceutical compositions comprising an effective memory enhancing amount of such a compound.

143 Claims, No Drawings

9-AMINO-1,2,3,4-TETRAHYDROACRIDIN-1-OL AND RELATED COMPOUNDS

This invention relates to compounds having the formula

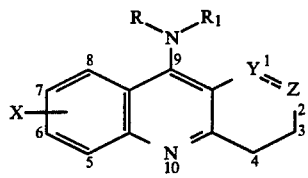

wherein X is hydrogen, loweralkyl, loweralkoxy, halogen, hydroxy, nitro, $NHCOR_2$ wherein $R_2$ is loweralkyl, or a group of the formula $NR_3R_4$ wherein $R_3$ and $R_4$ are independently hydrogen or loweralkyl; R and $R_1$ are independently hydrogen, loweralkyl, phenylloweralkyl, phenylloweralkyl in which the phenyl group is substituted by one or more loweralkyl, loweralkoxy, halogen, hydroxy or trifluoromethyl, diphenylloweralkyl or diphenylloweralkyl in which one or both phenyl groups are substituted by one or more loweralkyl, loweralkoxy, halogen, hydroxy or trifluoromethyl; Y is C=O or $CR_5OH$ wherein $R_5$ is hydrogen or loweralkyl; Z is $CH_2$ or $C=CR_6R_7$ wherein $R_6$ and $R_7$ are independently hydrogen or loweralkyl; or Y and Z taken together is $CR_5=CH$ wherein $CR_5$ and CH correspond to Y and Z respectively; an optical antipode thereof, or a pharmaceutically acceptable acid addition salt thereof, which are useful for enhancing memory, methods for synthesizing them, and pharmaceutical compositions comprising an effective memory enhancing amount of such a compound.

This invention also relates to compounds having the formula

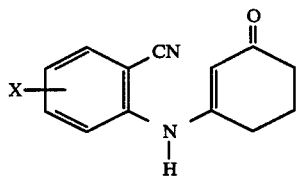

where X is as defined above which are useful as intermediate compounds for synthesizing the compounds of Formula I and a method for synthsizing them.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chorine, bromine or iodine.

The compounds of this invention are prepared by following one or more of the steps described below. Throughout the description of the synthetic steps, definitions of X, Y, Z, R and $R_1$ through $R_7$ are as given above unless otherwise stated or indicated.

STEP A

Compounds of Formula II are prepared by reacting a compound of Formula III with 1,3-cyclohexadione. Typically, said reaction is conducted in a suitable solvent such as an etheral solvent including tetrahydrofuran, diethyl ether and dioxane at a temperature of about 30°–100° C.

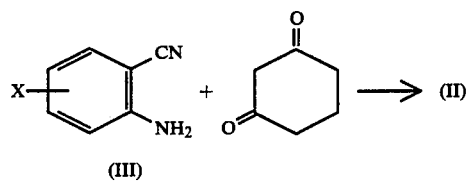

STEP B

Compounds of Formula IV are prepared by cyclizing a compound II in the presence of a metallic halide such as cuprous chloride, cuprous bromide or cuprous iodide and the like used as a catalyst. Typically said cyclization reaction is conducted in a suitable solvent such as an ethereal solvent including tetrahydrofuran, diethyl ether and dioxane and in the presence of a catalyst and a basic inorganic salt such as potassium carbonate, potassium bicarbonate, sodium carbonate, sodium bicarbonate or the like, at a temperature of about 30°–100° C.

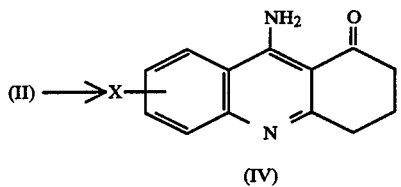

STEP C

Compounds of Formula V (where $R_1$ is not hydrogen and X is not OH, $NHCOR_2$, amino or loweralkylamino) are prepared by reacting compound IV with a compound of the formula $R_1W$, W being Cl, Br, I or $OSO_3CH_3$ (mesyloxy). Typically, said reaction is conducted in a biphasic system comprising a suitable organic solvent such as dichloromethane, chloroform, benzene, toluene or the like, a strongly alkaline aqueous phase such as 50% aqueous NaOH or the like, the starting compounds and a phase transfer catalyst such as tetrabutylammonium hydrogensulfate at a temperature of about 0°–50° C.

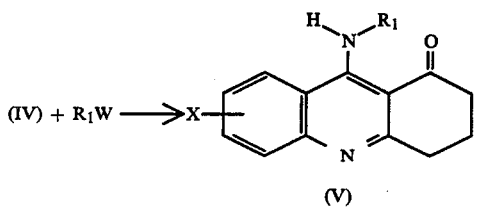

(IV) + $R_1W \longrightarrow$ (V)

$R_1 \neq H$
$X \neq OH$, $NHCOR_2$, amino or loweralkylamino

Where X is OH, the excluded compounds can be prepared by subjecting a compound of Formula V where X is a loweralkoxy group (e.g. methoxy group) to a cleavage reaction conducted, for instance, with the aid of pyridine hydrochloride at a temperature of around 180° C.

Where X is amino, the excluded compounds can be prepared from a compound of Formula V where X is hydrogen by successively conducting nitration and hydrogenation in substantially the same manner as described below as STEPS E and F, respectively.

Where X is $NHCOR_2$, the excluded compounds can be obtained by subjecting the corresponding amino compounds (X=$NH_2$) obtained above to an acylation reaction using, for instance, $(R_2CO)_2O$ in substantially the same manner as described below as STEP G.

Where X is loweralkylamino, the excluded compounds can be prepared by reacting the corresponding acylamino compounds (X=$NHCOR_2$) obtained above with a loweralkyl iodide or bromide of the formula $R_3I$ or $R_3Br$ where $R_3$ is loweralkyl in the presence of an inorganic base such as KOH or the like, and hydrolyzing the resultant product where X is

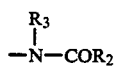

in a routine manner.

STEP D

In a manner similar to the one described above as STEP C, compounds of Formula VI (where neither of $R_1$ and R is hydrogen and X is not OH, $NHCOR_2$, amino or loweralkylamino) are obtained by further reacting compound V with a compound RW, W being the same as defined above.

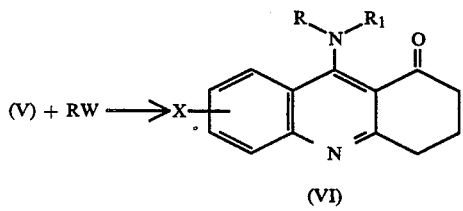

(V) + RW $\longrightarrow$ (VI)

$R_1 \neq H$, $R \neq H$
$X \neq OH$, $NHCOR_2$, amino or loweralkylamino

Where X is OH, $NHCOR_2$, amino or loweralkylamino, the excluded compounds can be obtained by use of the reaction schemes described above in STEP C for preparing compounds V where X is OH, $NHCOR_2$, amino or loweralkylamino, respectively.

STEP E

Compounds of Formula VII (namely compounds of Formula IV, V or VI where X is 7-$NO_2$ and R and $R_1$ are hydrogen or loweralkyl) may be prepared by the nitration of a compound of Formula VIII. Said nitration occurs with a good selectivity at the 7-position of the ring. Said reaction is typically conducted in the presence of concentrated sulfuric acid and nitric acid at a temperature of from about $-10°$ to about 30° C.

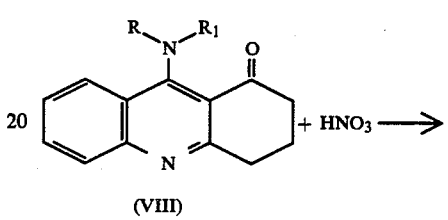

(VIII) + $HNO_3 \longrightarrow$ (VII)

STEP F

Compounds of Formula IX are prepared by the hydrogenation of compound VII in the presence of hydrogen gas and a suitable catalyst such as for instance a noble metal including palladium, platinum, rhodium or the like. Typically, said hydrogenation is conducted in a suitable medium such as glacial acetic acid, ethanol or the like under a suitable hydrogen gas pressure such as about 10–60 psig at a temperature of about 20°–40° C.

(VII) + $H_2$, Pd/C $\longrightarrow$

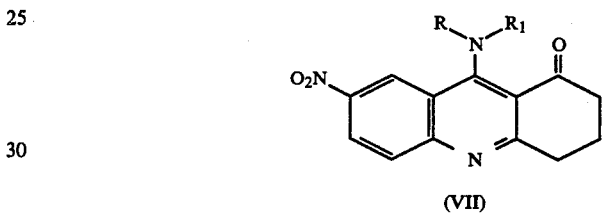

(IX)

STEP G

Compounds of Formula X are prepared by reacting compound IX with a suitable acylating agent such as an acid anhydride of the formula $(R_2CO)_2O$ or the like in a suitable solvent such as a carboxylic acid of the formula $R_2COOH$. Typically said reaction is conducted at a temperature of about 80°–120° C.

(IX) + $(R_2CO)_2O \longrightarrow$

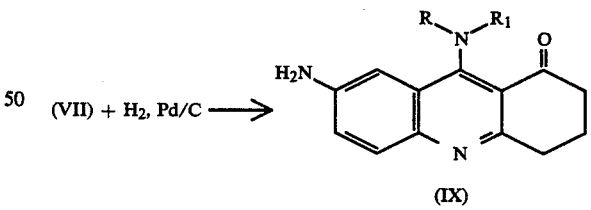

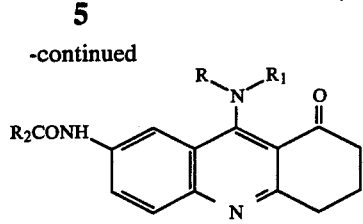

(X)

STEP H

Compounds of Formula XI (where X is not NHCOR$_2$ or NO$_2$) are prepared by reacting a compound of Formula XII obtained from one of the foregoing STEPS A through G with a suitable metal hydride such as LiAlH$_4$ in a suitable solvent such as an ethereal solvent including tetrahydrofuran, diethyl ether, dioxane and mixtures thereof at a temperature of from about −20° to about 20° C., and thereafter hydrolyzing the product.

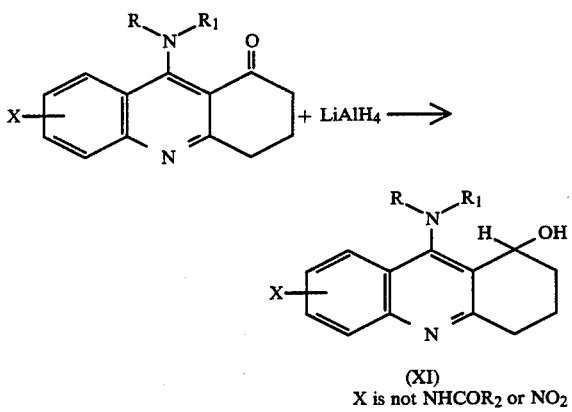

(XI)
X is not NHCOR$_2$ or NO$_2$

Where X is NO$_2$, the excluded compounds can be prepared by reducing compounds XII where X is NO$_2$ with NaBH$_4$ in a suitable medium such as acetic acid, hydrochloric acid or phosphoric acid aqueous solution.

STEP I

Compounds of Formula XIII (where X is not NHCOR$_2$) are prepared by reacting compound XII with a suitable organometallic compound such as a compound of the formula R$_5$Li (where R$_5$ is loweralkyl) in a suitable solvent such as an ethereal solvent including tetrahydrofuran, diethyl ether and dioxane at a temperature of about 10°–50° C. Subsequent to the reaction of compound XII with R$_5$Li, the resultant product is hydrolyzed to obtain compound XIII.

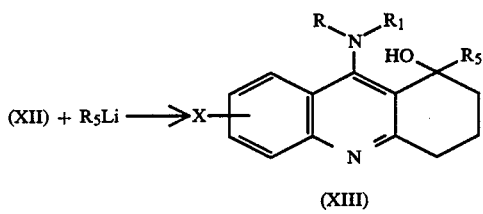

(XIII)

R$_5$ is loweralkyl
X ≠ NHCOR$_2$

Where X is NHCOR$_2$ in the above STEPS H or I, the excluded compounds can be prepared in general by use of the above reaction STEPS A through I in a different sequence. For example, compounds of Formula XI-a below can be prepared by use of the sequence depicted below.

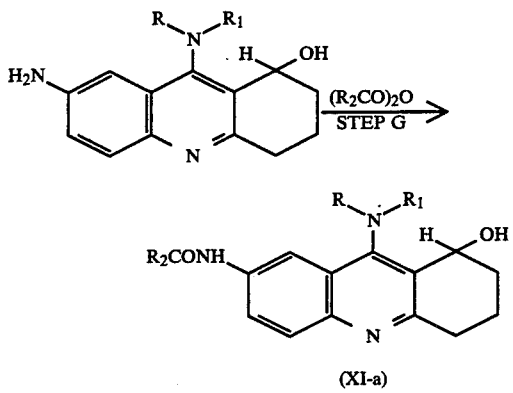

(XI-a)

STEP J

Compounds of Formula XIV are prepared by first reacting compound XII with a compound of Formula XV to obtain an intermediate compound of Formula XVI and then converting the latter to compound XIV. The first reaction is conducted typically in a sutiable medium such as trifluoroacetic acid, acetic anhydride or an alcohol plus hydrochloric acid at a temperature of about 70°–120° C. The second reaction is conducted typically in a suitable solvent such as toluene, benzene or the like at a temperature of about 80°–120° C.

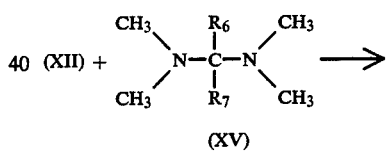

(XV)

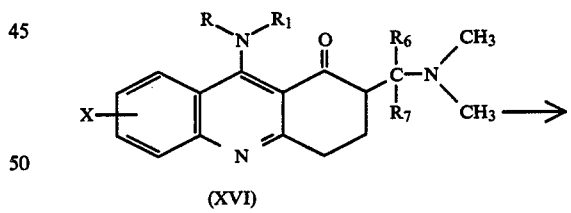

(XVI)

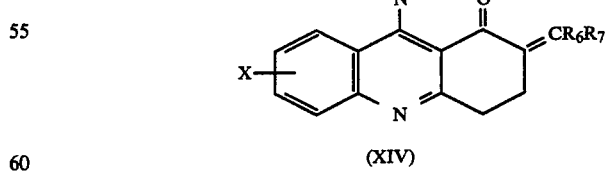

(XIV)

STEP K

Compounds of Formula XVII are prepared by the dehydration rection of compound XI or XIII obtained from STEP H or I above. Typically, said dehydration is conducted in the presence of a suitable solvent such as glacial acetic acid, dimethylformamide, dimethyl sulfoxide or the like and a small amount of acid such as sulfuric acid at a temperature of about 70°–120° C.

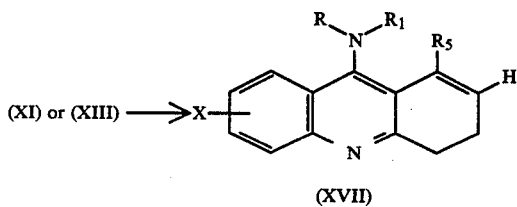

(XVII)

STEP L

Compounds of Formula XVIII (where X is not NHCOR$_2$ or NO$_2$ and R$_5$ is H or loweralkyl) may be prepared by reacting compound XIV with (i-Bu)$_2$AlH or R$_5$Li (R$_5$ is loweralkyl) in the same manner as described in STEP H or I, respectively.

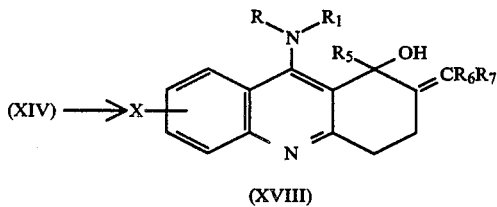

(XVIII)

X ≠ NHCOR$_2$, NO$_2$

The acridines of the present invention are useful in the treatment of various memory dysfunctions characterized by decreased cholinergic function, such as Alzheimer's disease.

This utility is manifested by the ability of these compounds to inhibit the enzyme cholinesterase and thereby increase acetylcholine levels in the brain.

Additionally, some of the compounds of this invention exhibit antidepressant activities, which activities being particularly helpful for patients suffering from Alzheimer's disease. Further, the compounds of this invention are in general less toxic than heretofore known compounds such as tacrine and physostigmine, making them more therapeutically acceptable.

Cholinesterase Inhibition Assay

The ability to inhibit acetylcholinesterase was determined by the photometric method of Ellman et al., Biochem. Pharmacol. 7, 88 (1961).

| Compound | Cholinesterase Inhibition IC$_{50}$(molar) |
|---|---|
| 9-Amino-3,4-dihydroacridin-1(2H)—one | $2.5 \times 10^{-4}$ |
| 3,4-Dihydro-9-(4,4-diphenylbutyl)-aminoacridin-1(2H)—one | $1.3 \times 10^{-5}$ |
| 9-Amino-1,2,3,4-tetrahydroacridin-1-ol | $2.3 \times 10^{-5}$ |
| 9-Phenethylamino-1,2,3,4-tetrahydroacridin-1-ol | $2.4 \times 10^{-4}$ |
| 9-Amino-3,4-dihydroacridine (prior art compounds) | $6.5 \times 10^{-6}$ |
| 9-Amino-1,2,3,4-tetrahydroacridine (tacrine) | $5.7 \times 10^{-6}$ |
| Physostigmine | $9.2 \times 10^{-8}$ |

This utility is further demonstrated by the ability of these compounds to restore cholinergically deficient memory in the Dark Avoidance Assay, where they are in general active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scolopamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose (mg/kg of Body Weight) | % of Animals Greater than Scopolamine |
|---|---|---|
| 9-Amino-1,2,3,4-tetrahydroacridin-1-ol | 0.63 | 33 |
| 9-Benzylamino-1,2,3,4-tetrahydroacridin-1-ol | 1.25 | 27 |
| 9-Amino-3,4-dihydroacridine (prior art compounds) | 2.50 | 20 |
| Tacrine | 0.63 | 13 |
| Pilocarpine | 5.0 | 13 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, aline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
2-(3-Oxocyclohexen-1-yl)aminobenzonitrile;
4-Chloro-2-(3-oxocyclohexen-1-yl)aminobenzonitrile;
9-Amino-3,4-dihydroacridin-1(2H)-one;
9-Benzylamino-3,4-dihydroacridin-1(2H)-one;
3,4-Dihydro-9-(methylamino)acridin-1(2H)-one;
9-Amino-1,2,3,4-tetrahydroacridin-1-ol;
3,4-Dihydro-9-(n-propylamino)acridin-1(2H)-one;
9-Amino-3,4-dihydro-7-nitroacridin-1(2H)-one;
9-Methylamino-1,2,3,4-tetrahydroacridin-1-ol;
3,4-Dihydro-9-methylamino-7-nitroacridin-1(2H)-one;
9-(n-Propylamino)-1,2,3,4-tetrahydroacridin-1-ol;
9-Benzylamino 1,2,3,4-tetrahydroacridin-1-ol;
9-Amino-1-methyl-1,2,3,4-tetrahydroacridin-1-ol;
9-Amino-3,4-dihydro-2-methyleneacridin-1(2H)-one;
3,4-Dihydro-9-(2-fluorobenzylamino)acridin-1(2H)-one;
7,9-Diamino-3,4-dihydroacridin-1(2H)-one;
3,4-Dihydro-9-(phenethylamino)acridin-1(2H)-one;
9-Amino-3,4-dihydroacridine;
N-[9-Amino-3,4-dihydro-1(2H)-oxoacridin-7-yl]acetamide;
9-Amino-7-chloro-3,4-dihydroacridin-1(2H)-one;
3,4-Dihydro-9-(4,4-diphenylbutylamino)acridin-1(2H)-one;
9-(2-Fluorobenzylamino)-1,2,3,4-tetrahydroacridin-1-ol;
9-Phenethylamino-1,2,3,4-tetrahydroacridin-1-ol;
9-Amino-7-chloro-1,2,3,4-tetrahydroacridin-1-ol;
9-Amino-6-chloro-3,4-dihydroacridin-1(2H)-one;
9-Amino-6-chloro-1,2,3,4-tetrahydroacridin-1-ol;
9-(4,4-Diphenylbutylamino)-1,2,3,4-tetrahydroacridin-1-ol;
9-Amino-3,4-dihydro-7-methylacridin-1(2H)-one;
9-Amino-3,4-dihydro-7-methoxyacridin-1(2H)-one;
9-Amino-3,4-dihydro-7-hydroxyacridin-1(2H)-one;
7-Acetoxy-9-amino-3,4-dihydroacridin-1(2H)-one;
9-Amino-3,4-dihydro-7-fluoroacridin-1(2H)-one;
9-Amino-7-methyl-1,2,3,4-tetrahydroacridin-1-ol;
9-Amino-7-methoxy-1,2,3,4-tetrahydroacridin-1-ol;
9-Amino-7-hydroxy-1,2,3,4-tetrahydroacridin-1-ol;
7-Acetoxy-9-amino-1,2,3,4-tetrahydroacridin-1-ol;
9-Amino-7-fluoro-1,2,3,4-tetrahydroacridin-1-ol;
3,4-Dihydro-7-methyl-9-(methylamino)acridin-1(2H)-one;
3,4-Dihydro-7-methoxy-9-(methylamino)acridin-1(2H)-one;
7-Methyl-9-methylamino-1,2,3,4-tetrahydroacridin-1-ol;
7-Methoxy-9-methylamino 1,2,3,4-tetrahydroacridin-1-ol;
9-Benzylamino-3,4-dihydro-7-methylacridin-1(2H)-one;
9-Benzylamino-3,4-dihydro-7-methoxyacridin-1(2H)-one;
9-Benzylamino-7-methyl-1,2,3,4-tetrahydroacridin-1-ol;
9-Benzylamino-7-methoxy-1,2,3,4-tetrahydroacridin-1-ol;
3,4-Dihydro-7-methyl-9-(phenethylamino)acridin-1(2H)-one;
3,4-Dihydro-7-methoxy-9-(phenethylamino)acridin-1(2H)-one;
7-Methyl-9-phenethylamino-1,2,3,4-tetrahydroacridin-1-ol;
7-Methoxy-9-phenethylamino-1,2,3,4-tetrahydroacridin-1-ol;
7-Chloro-3,4-dihydro-9-(methylamino)acridin-1(2H)-one;
7-Chloro-3,4-dihydro-9-(phenethylamino)acridin-1(2H)-one;
9-Benzylamino-7-chloro-3,4-dihydroacridin-1(2H)-one;
7-Chloro-9-methylamino 1,2,3,4-tetrahydroacridin-1-ol;
7-Chloro-9-phenethylamino-1,2,3,4-tetrahydroacridin-1-ol;
9-Benzylamino-7-chloro-1,2,3,4-tetrahydroacridin-1-ol;
6-Chloro-3,4-dihydro-9-(methylamino)acridin-1(2H)-one;
6-Chloro-3,4-dihydro-9-(phenethylamino)acridin-1(2H)-one;
9-Benzylamino-6-chloro-3,4-dihydroacridin-1(2H)-one;
6-Chloro-9-methylamino-1,2,3,4-tetrahydroacridin-1-ol;
6-Chloro-9-phenethylamino-1,2,3,4-tetrahydroacridin-1-ol;
9-Benzylamino-6-chloro-1,2,3,4-tetrahydroacridin-1-ol;
9-Amino-3,4-dihydro-7-(dimethylamino)acridin-1(2H)-one;

9-Amino-3,4-dihydro-2-isopropylideneacridin-1(2H)-one;
9-Amino-3,4-dihydro-1-methylacridine;
3,4-Dihydro-9-(4,4-diphenylbutylamino)-7-methylacridin-1(2H)-one;
3,4-Dihydro-9-(4,4-diphenylbutylamino)-7-methoxyacridin-1(2H)-one;
6-Chloro-3,4-dihydro-9-(4,4-diphenylbutylamino)acridin-1(2H)-one;
7-Chloro-3,4-dihydro-9-(4,4-diphenylbutylamino)acridin-1-(2H)-one;
3,4-Dihydro-9-(3-phenoxypropylamino)acridin-1(2H)-one;
9-(4,4-diphenylbutylamino)-7-methyl-1,2,3,4-tetrahydroacridin-1-ol;
9-(4,4-diphenylbutylamino)-7-methoxy-1,2,3,4-tetrahydroacridin-1-ol;
6-Chloro-9-(4,4-diphenylbutylamino)-1,2,3,4-tetrahydroacridin-1-ol;
7-Chloro-9-(4,4-diphenylbutylamino)-1,2,3,4-tetrahydroacridin-1-ol;
9-(3-phenoxypropylamino)-1,2,3,4-tetrahydroacridin-1-ol;
3,4-Dihydro-9-(3-fluorobenzylamino)acridin-1(2H)-one;
3,4-Dihydro-9-(4-fluorobenzylamino)acridin-1(2H)-one;
9-(2-chlorobenzylamino)-3,4-dihydroacridin-1(2H)-one;
9-(2-chlorobenzylamino)-3,4-dihydroacridin-1(2H)-one;
3,4-Dihydro-9-(4-methoxybenzylamino)acridin-1(2H)-one;
9-(4-chlorobenzylamino)-3,4-dihydroacridin-1(2H)-one;
3,4-Dihydro-9-(3-methylbenzylamino)acridin-1(2H)-one;
3,4-Dihydro-9-(4-methylbenzylamino)acridin-1(2H)-one;
3,4-Dihydro-9-(2-trifluoromethylbenzylamino)acridin-1(2H)-one;
3,4-Dihydro-9-(3-trifluoromethylbenzylamino)acridin-1(2H)-one;
3,4-Dihydro-9-(4-trifluoromethylbenzylamino)acridin-1(2H)-one;
9-(2,4-Difluorobenzylamino)-3,4-dihydroacridin-1(2H)-one;
9-(3,4-Difluorobenzylamino)-3,4-dihydroacridin-1(2H)-one;
3,4-Dihydro-9-(3,4-dimethoxybenzylamino)acridin-1(2H)-one
9-(3-Fluorobenzylamino)-1,2,3,4-tetrahydroacridin-1-ol;
9-(4-Fluorobenzylamino)-1,2,3,4-tetrahydroacridin-1-ol;
9-(2-Chlorobenzylamino)-1,2,3,4-tetrahydroacridin-1-ol;
9-(3-Chlorobenzylamino)-1,2,3,4-tetrahydroacridin-1-ol;
9-(4-Chlorobenzylamino)-1,2,3,4-tetrahydroacridin-1-ol;
9-(2-Methoxybenzylamino)-1,2,3,4-tetrahydroacridin-1-ol;
9-(3-Methoxybenzylamino)-1,2,3,4-tetrahydroacridin-1-ol;
9-(4-Methoxybenzylamino)-1,2,3,4-tetrahydroacridin-1-ol;
9-(2-Methylbenzylamino)-1,2,3,4-tetrahydroacridin-1-ol;
9-(3-Methylbenzylamino)-1,2,3,4-tetrahydroacridin-1-ol;
9-(4-Methylbenzylamino)-1,2,3,4-tetrahydroacridin-1-ol;
9-(2-Trifluoromethylbenzylamino)-1,2,3,4-tetrahydroacridin-1-ol;
9-(3-Trifluoromethylbenzylamino)-1,2,3,4-tetrahydroacridin-1-ol;
9-(4-Trifluoromethylbenzylamino)-1,2,3,4-tetrahydroacridin-1-ol;
9-(2,4-Difluorobenzylamino)-1,2,3,4-tetrahydroacridin-1-ol;
9-(3,4-Difluorobenzylamino)-1,2,3,4-tetrahydroacridin-1-ol;
9-(3,4-Dimethoxybenzylamino)-1,2,3,4-tetrahydroacridin-1-ol;

The following examples are given for illustrative purposes and are not to be considered as limiting the invention disclosed herein. All temperatures are given in degrees Celsius.

EXAMPLE 1

2-(3-oxocyclohexen-1-yl)aminobenzonitrile

In 1.5 liters of tetrahydrofuran was added 98.32 g of anthranilonitrile. The mixture was made acidic to litmus with concentrated HCl and with mechanical stirring was warmed to reflux. To the refluxing solution was added dropwise a solution containing 93.3 g (1 eg) of 1,3-cyclohexadione in 700 ml of tetrahydrofuran. After the addition was complete the reaction mixture was refluxed 0.5 hour more, then cooled and filtered to yield 161 g (91%) of product as an HCl salt, melting point 206° C. A portion of the product was first washed with 10% $Na_2CO_3$ (thus converting it to a free base) and then recrystallized from dichloromethane/hexanes to yield a powder, melting point 210° C.

ANALYSIS: Calculated for $C_{13}H_{12}N_2O$: 73.57% C; 5.70% H; 13.20% N. Found: 73.44% C; 5.79% H; 13.20% N.

EXAMPLE 2

4-Chloro-2-(3-oxocyclohexen-1-yl)aminobenzonitrile hydrochloride

In 75 ml of tetrahydrofuran was dissolved 5.00 g of 2-amino-4-chlorobenzonitrile. Into the mechanically stirred solution was bubbled HCl gas until a slurry was formed. The gas was disconnected and the slurry was brought to reflux. To the refluxing slurry was added dropwise over 10 minutes a solution containing 3.67 g (1.1 eq) of 1,3-cyclohexadione in 75 ml of tetrahydrofuran. Reflux was continued for 0.5 hour during which the reaction went to completion. The slurry was cooled and filtered and the filter cake washed with tetrahydrofuran to yield 8.87 g (96%) of a solid, melting point 229° C. (with decomposition).

ANALYSIS: Calculated for $C_{13}H_{11}ClN_2O.HCl$: 55.13% C; 4.27% H; 9.89% N. Found: 55.35% C; 4.55% H; 9.74% N.

EXAMPLE 3

9-Amino-3,4-dihydroacridin-1(2H)-one

In 2 liters of tetrahydrofuran were combined 219.3 g of 2-(3-oxocyclohexen-1-yl)aminobenzonitrile hydrochloride, 250 g (2 eq) of milled $K_2CO_3$, and 3 g of CuCl catalyst. The mechanically stirred mixture was refluxed 5 hours and then filtered hot to remove the inorganic salts. The filtrate was evaporated to a residue and the residue was recrystallized twice from isopropanol to yield 77.4 g (41%) of a powder, melting point 236°–238° C.

ANALYSIS: Calculated for $C_{13}H_{12}N_2O$: 73.57% C; 5.70% H; 13.20% N. Found: 73.37% C; 5.83% H; 13.20% N.

EXAMPLE 4

9-Benzylamino-3,4-dihydroacridin-1(2H)-one

In a biphasic solution consisting of 150 ml of dichloromethane and 100 ml of 50% aqueous NaOH were added 4.00 g of 9-amino-3,4-dihydroacridin-1(2H)-one, and 0.96 g of tetrabutylammonium hydrogensulfate catalyst. The mixture was stirred mechanically for 0.5 hour and thereafter 2.47 ml (1.1 eq) of benzyl bromide was added in one portion. After 4 hours of vigorous stirring, the reaction appeared complete based on thin layer chromatography analysis. The reaction mixture was poured into water/ice and the dichloromethane layer separated, dried over $MgSO_4$ and evaporated to a solid. the solid was recrystallized three times from dichloromethane/hexanes to yield 2.35 g (41%) of product, melting point 162°–163° C.

ANALYSIS: Calculated for $C_{20}H_{18}N_2O$: 79.44% C; 6.00% H; 9.25% N. Found: 79.43% C; 6.11% H; 9.31% N.

EXAMPLE 5

3,4-Dihydro-9-(methylamino)acridin-1(2H)-one

In 150 ml of dichloromethane and 100 ml of 50% NaOH were added 5.00 g of 9-amino-3,4-dihydroacridin-1(2H)-one and 0.80 g (0.1 eq) of tetrabutylammonium hydrogensulfate. The biphasic mixture was mechanically stirred for 0.5 hour and thereafter 4.4 ml (3 eq) of $CH_3I$ was added. The reaction mixture was stirred overnight. Analysis of the reaction mixture indicated that the starting material was completely consumed. The reaction mixture was poured into cold water and the dichloromethane layer was evaporated, dried over $MgSO_4$ and filtered through alumina and the solvent was evaporated to afford a solid. The solid was recrystallized from dichloromethane/hexanes to yield 3.73 g (70%) of crystalline product after drying, melting point 116°–117° C.

ANALYSIS: Calculated for $C_{14}H_{14}N_2O$: 74.31% C; 6.24% H; 12.38% N. Found: 74.04% C; 6.40% H; 12.37% N.

EXAMPLE 6

9-Amino-1,2,3,4-tetrahydroacridin-1-ol

In 100 ml of dry tetrahydrofuran was added 5.00 g of 9-amino-3,4-dihydroacridin-1(2H)-one. The mechanically stirred suspension was cooled to −5° C. and 21.4 ml (1.0 eq) of 1.1M $LiAlH_4$ solution in ether was added dropwise. After completion of the addition, the reaction mixture was stirred further for 2 hours, whereupon the reaction appeared complete based on thin layer chromatography analysis. The $LiAlH_4$ was neutralized with 2 ml of saturated $NH_4Cl$ and the salts were dissolved with 30% potassium hydroxide. The insoluble product was filtered off and rinsed with water. The precipitate was then dissolved in 3N HCl and the residual insoluble salts filtered off. The acid solution was washed with EtOAc and made basic (pH 9) with 10% NaOH. The precipitated product was filtered and washed with water. After drying at 80° C. under vacuum overnight, 4.15 g (82%) of a powder was obtained, melting point 245° C.

ANALYSIS: Calculated for $C_{13}H_{14}N_2O$: 72.87% C; 6.58% H; 13.07% N. Found: 72.57% C; 6.71% H; 13.00% N.

EXAMPLE 7

3,4-Dihydro-9-(n-propylamino)acridin-1(2H)-one

In a mixture consisting of 150 ml of dichloromethane and 100 ml of 50% NaOH were combined 5.00 g of 9-amino-3,4-dihydroacridin-1(2H)-one and 0.80 g (0.10 eq) of tetrabutylammonium hydrogensulfate. The biphasic mixture was stirred for 0.5 hour and thereafter 6.9 ml (3 eq) of n-propyl iodide was added and the stirring at room temperature was continued for 2 days during which three more portions of the above quantities of the alkylating agent were added at 12 hour intervals. The reaction was then complete based on thin layer chromatography analysis. The organics were separated and purified by passing through an alumina column (dichloromethane). The product was recrystallized from dichloromethane/$Et_2O$ to yield 3.77 g (63%) of a solid, melting point 145° C.

ANALYSIS: Calculated for $C_{16}H_{18}N_2O$: 75.56% C; 7.13% H; 11.01% N. Found: 75.72% C; 7.05% H; 11.02% N.

EXAMPLE 8

9-Amino-3,4-dihydro-7-nitoracridin-1(2H)-one

To 100 ml of cold $H_2SO_4$ was added 5.00 g of 9-amino-3,4-dihydroacridin-1(2H)-one. The mechanically stirred solution was cooled to 0° C. and 2.1 ml (1 eq) of concentrated $HNO_3$ (70 wt % solution) was added dropwise. Stirring was continued for 15 minutes after the addition, whereupon the reaction was complete. The reaction mixture was poured into excess crushed ice and made basic with a slight excess of 50% NaOH solution. More ice was added during the neutralization to keep the solution cool. The resulting precipitate was filtered and chromatographed over silica gel (EtOAc). The fractions containing the product were evaporated to a solid which was triturated with pentane to yield 4.77 g (79%) of a solid after drying, melting point 254° C. (with decomposition).

ANALYSIS: Calculated for $C_{13}N_{11}N_3O_3$: 60.70% C; 4.31% H; 16.33% N. Found: 60.80% C; 4.36% H; 16.38% N.

EXAMPLE 9

9-Methylamino-1,2,3,4-tetrahydroacridin-1-ol

In 50 ml of dry tetrahydrofuran was dissolved 8.00 g of 3,4-dihydro-9-(methylamino)acridin-1(2H)-one. The mechanically stirred solution was cooled to −10° C. under $N_2$ and 32 ml (1 eq) of 1.1M $LiAlH_4$ solution in ether was added over 5 minutes. The stirring was continued for 45 minutes after the addition, during which the reaction went to completion. The excess $LiAlH_4$ was neutralized with 1 ml of saturated $NH_4Cl$ and the resulting salts dissolved in 30% potassium hydroxide solution. The tetrahydrofuran solution was separated and evaporated to an oil which solidified upon trituration with 1:1 dichloromethane/hexanes. The solid was recrystallized from 10:1 hexanes/tetrahydrofuran to yield 5.89 g (73%) of a solid, melting point 160°–161° C.

ANALYSIS: Calculated for $C_{14}H_{16}N_2O$: 73.65% C; 7.06% H; 12.27% N. Found: 73.61% C; 7.00% H; 12.39% N.

EXAMPLE 10

3,4-Dihydro-9-methylamino-7-nitroacridin-1(2H)-one

In 100 ml of concentrated $H_2SO_4$ at 0° C. was added 4.83 g of 3,4-dihydro-9-(methylamino)acridin-1(2H)-one. While maintaining the reaction at 0° C., 1.92 ml (1 eq) of concentrated $HNO_3$ (70 wt %) was added dropwise over 10 minutes. Since the reaction appeared complete after the addition based on thin layer chromatography, the reaction mixture was poured into ice and neutralized with 50% NaOH. At the basic point a precipitate formed. This was filtered and chromatographed on silica gel (EtOAc) and the product was recrystallized from dichloromethane/hexanes to yield 2.75 g (47%) of a solid, melting point 208° C.

ANALYSIS: Calculated for $C_{14}H_{13}N_3O_3$: 61.99% C; 4.83% H; 15.49% N. Found: 61.87% C; 4.79% H; 15.28% N.

EXAMPLE 11

9-(n-Propylamino)-1,2,3,4-tetrahydroacridin-1-ol

In 50 ml of dry tetrahydrofuran was suspended 2.49 g of 3,4-dihydro-9-(n-propylamino)acridin-1(2H)-one. The mechanically stirred suspension was cooled in ice and 4.50 ml (0.5 eq) of 1.1 M $LiAlH_4$ solution in ether was added dropwise, whereupon a solution formed. After the addition, the reaction appeared complete based on thin layer chromatography analysis. The excess hydride was neutralized with 0.5 ml of saturated $NH_4Cl$ solution and thereafter 30% potassium hydroxide was added to dissolve the salts. The supernatent tetrahydrofuran solution was separted and evaporated to a solid. The solid was recrystallized from 1:4 dichloromethane/EtOAc to yield 1.88 g (75%) of needles, melting point 164° C.

ANALYSIS: Calculated for $C_{16}H_{20}N_2O$: 74.97% C; 7.86% H; 10.93% N. Found: 75.02% C; 7.86% H; 10.93% N.

EXAMPLE 12

9-Benzylamino-1,2,3,4-tetrahydroacridin-1-ol

In 75 ml of dry tetrahydrofuran was dissolved 3.81 g of 9-benzylamino-3,4-dihydroacridin-1(2H)-one with mechanical stirring. The solution was cooled in ice under $N_2$ and 5.9 ml (0.5 eq) of 1.1M $LiAlH_4$ solution in ether was added dropwise. After 0.5 hour the reaction was complete based on thin layer chromatography analysis. The excess hydride was neutralized with 0.5 ml of saturated $NH_4Cl$ solution and the inorganic salts were extracted into 30% potassium hydroxide. The tetrahydrofuran solution was decanted and evaporated to a solid which was recrystallized from 1:10 dichloromethane/EtOAc to yield 2.89 g (75%) of a solid, melting point 159° C.

ANALYSIS: Calculated for $C_{20}H_{20}N_2O$: 78.92% C; 6.62% H; 9.20% N; Found: 78.77% C; 6.88% H; 9.20% N.

EXAMPLE 13

9-Amino-1-methyl-1,2,3,4-tetrahydroacridin-1-ol

In 100 ml of dry tetrahydrofuran was suspended 5.00 g of 9-amino-3,4-dihydroacridin-1(2H)-one at ice temperature and 78 ml (4 eq) of 1.2M $CH_3Li$ solution in ether was added thereto at such a rate as to avoid bubbling. The reaction mixture was stirred overnight as it warmed to ambient temperature. The next day 20 ml more of the $CH_3Li$ solution was added to drive the reaction to a completion. After 0.5 hour the reaction was quenched with excess water and 4.97 g of the precipitate was collected and air dried. The product was recrystallized from MeOH/toluene. The yield was 2.06 g (38%) of granules, melting point 250° C.

ANALYSIS: Calculated for $C_{14}H_{16}N_2O$: 73.65% C; 7.06% H; 12.27% N. Found: 73.43% C; 7.19% H; 12.19% N.

EXAMPLE 14

9-Amino-3,4-dihydro-2-methyleneacridin-1(2H)-one

In 25 ml of trifluoroacetic acid cooled in ice was dissolved 5.00 g of 9-amino-3,4-dihydroacridin-1(2H)-one. To the solution was added dropwise 6.70 ml (2.09 eq) of bisdimethylaminomethane over 5 minutes and thereafter the mixture was maintained at 90°–100° C. for 5 hours during which the starting material was converted to a mixture of intermediate and exo-methylene products. The reaction mixture was poured into ice/NaOH to make it basic and the precipitate was extracted with several portions of 5:1 dichloromethane/MeOH. The combined extracts were evaporated to a residue. The residue was refluxed in toluene for 5 hours during which the intermediate was converted to the end product. The reaction mixture was evaporated to a residue which was purified by chromatography on silica gel (EtOAc) to yield about 2 g of a solid. This was recrystallized from dichloromethane/EtOAc to yield 1.79 g (34%) of product as a solid, melting point 192°–193° C.

ANALYSIS: Calculated for $C_{14}H_{12}N_2O$: 74.98% C; 5.39% H; 12.49% N. Found: 75.28% C; 5.50% H; 12.59% N.

EXAMPLE 15

3,4-Dihydro-9-(2-fluorobenzylamino)acridin-1(2H)-one

In a mixture consisting of 150 ml of dichloromethane and 100 ml of 50% NaOH were combined 5.00 g of 9-amino-3,4-dihydroacridin-1(2H)-one, 3 ml (1 eq) of 2-fluorobenzylchloride and 1.20 g (0.15 eq) of tetrabutylammonium hydrogen sulfate. The biphasic mixture was mechanically stirred overnight and 3 ml of 2-fluorobenzylchloride was again added. After 4 hours of further stirring, the reaction was complete based on thin layer chromatography. The reaction mixture was partitioned between water and dichloromethane and the dichloromethane layer was separated, dried over $MgSO_4$, filtered and evaporated to a solid. The solid was purified by chromatography on silica gel (EtOAc) and the resultant product was recrystallized from 1:4 EtOAc/toluene to yield 4.09 g (54%) of a solid, melting point 163.5°–164° C.

ANALYSIS: Calculated for $C_{20}H_{17}FN_2O$: 74.98% C; 5.35% H; 8.74% N. Found: 74.80% C; 5.42% H; 8.76% N.

EXAMPLE 16

7,9-Diamino-3,4-dihydroacridin-1(2H)-one

In 250 ml of glacial acetic acid was dissolved 4.43 g of 9-amino-3,4-dihydro-7-nitroacridin-1(2H)-one and 0.44 g of 10% Pd/C was added. The mixture was put in a 500 ml hydrogenation vessel (Parr) and was shaken under 55 psig (initial) $H_2$. The uptake of $H_2$ was 3 eq before the reaction as complete. The reaction was poured into ice and made basic with 10% NaOH. The precipitate was filtered and dissolved in MeOH. The insoluble Pd/C catalyst was filtered off and the filtrate was diluted with toluene and concentrated until crystallization occurred. The yield was 2.84 g (73%) of a solid, melting point 310° C.

ANALYSIS: Calculated for $C_{13}H_{13}N_3O$: 68.70% C; 5.77% H; 18.49% N. Found: 68.48% C; 5.90% H; 18.48% N.

EXAMPLE 17

3,4-Dihydro-9-(phenethylamino)acridin-1(2H)-one

In a mixture consisting of 300 ml of dichloromethane and 200 ml of 50% NaOH were combined 10.00 g of 9-amino-3,4-dihydroacridin-1(2H)-one, 28 ml (6 eq) of 2-phenethyl bromide, and 3 g (0.2 eq) of tetrabutylammonium hydrogensulfate catalyst. The mixture was mechanically stirred for 4 days, during which 28 ml of 2-phenethyl bromide was added at intevals of 12 hours. After 4 days the reaction would go no further. The layers were separated and the dichloromethane layer was evaporated to an oil, which was extracted into 3N HCl and washed with EtOAc. The HCl solution was then made basic with 10% NaOH. The resulting precipitate was extracted into dichloromethane and the dichloromethane layer was evaporated to an oil containing mostly the starting material and the end product. The purification method was chromatography on silica gel with 20% EtOAc/dichloromethane solvent. The product thus obtained was recrystallized from dichloromethane/hexanes to yield 2.52 g (17%) of a solid, melting point 129°–132° C.

ANALYSIS: Calculated for $C_{21}H_{20}N_2O$: 79.72% C; 6.37% H; 8.85% N. Found: 79.78% C; 6.39% H; 8.98% N.

EXAMPLE 18

9-Amino-3,4-dihydroacridine hemihydrate

In 50 ml of HOAc was dissolved 3.00 g of 9-amino-1,2,3,4-tetrahydroacridin-1-ol. To this mechanically stirred solution at room temperature was added 0.75 ml (1 eq) of $H_2SO_4$. The reaction mixture was warmed on a steam bath causing a precipitate to form. After 0.5 hour of heating, the reaction was complete based on thin layer chromatography. The reaction mixture was poured into excess ice/10% NaOH and the precipitate was collected. The precipitate was dissolved in dichloromethane, dried over $MgSO_4$, filtered, and evaporated to a solid which was purified by silica gel chromatography to yield a solid. Two recrystallizations from dichloromethane/hexanes yielded 1.40 g (75% crude yield prior to chromatography) of a powder, melting point 178°–179° C.

ANALYSIS: Calculated for $C_{13}H_{12}N_2 \cdot \frac{1}{2}H_2O$: 76.07% C; 6.38% H; 13.65% N. Found: 76.64% C; 6.36% H; 13.73% N.

EXAMPLE 19

N-[9-amino-3,4-dihydro-1(2H)-oxoacridin-7-yl]acetamide

In 50 ml of glacial acetic acid was dissolved 3.00 g of 7,9-diamino-3,4-dihydroacridin-1(2H)-one. The mechanically stirred solution was cooled to 10° C. and 1.37 ml (1.1 eq) of acetic anhydride was added. The solution was then heated on the steam bath for 0.5 hour during which the reaction went to completion. The reaction mixture was poured into ice and made basic with 10% NaOH. The resulting emulsion was centrifuged and the supernatant decanted off. The solid was washed with water and recrystallized from 1:10 MeOH/toluene to yield 2.25 (63%) of a solid, melting point over 260° C.

ANALYSIS: Calculated for $C^{15}H^{15}N^3O^2$: 66.90% C; 5.61% H; 15.60% N. Found: 66.74% C; 5.81% H; 15.56% N.

EXAMPLE 20

9-Amino-7-chloro-3,4-dihydroacridin-1(2H)-one

In 5 liters of toluene were combined 200 ml of dimethylformamide, 180.71 g of 5-chloro-2-(3-oxocyclohexen-1-yl)aminobenzonitrile hydrochloride prepared in the same manner as the compounds of EXAMPLES 1 and 2, 176 g (2 eq) of milled $K_2CO_3$ and 3 g of cuprous chloride (CuCl). After 6 hours of reflux a little reaction occurred, so 3 g more of CuCl was added. After 12 hours of reflux more product had slowly formed. In order to hasten the reaction, 3 g more of CuCl was added. After overnight reflux the reaction mixture was evaporated and the residue extracted with dichloromethane via a Soxhlet extraction apparatus for 12 hours. The dichloromethane solution was evaporated to a solid. The solid was suspended in water and $H_2SO_4$ was added. The resultant salt which precipitated out, was filtered and made basic with 10% NaOH. The solid was filtered and recrystallized twice from isopropanol/toluene to yield 6.84 g (4%) of a solid, melting point over 260° C.

ANALYSIS: Calculated for $C_{13}H_{11}ClN_2O$: 63.27% C; 4.49% H; 11.35% N. Found: 63.42% C; 4.50% H; 11.28% N.

EXAMPLE 21

3,4-Dihydro-9-(4,4-diphenylbutylamino)acridin-1(2H)-one

In a mixture consisting of 480 ml of dichloromethane and 320 ml of 50% NaOH were combined 8.00g of 9-amino-3,4-dihydroacridin-1(2H)-one, 68 g (6 eq) of 1-mesyloxy-4,4-diphenylbutane and 2.56 g (0.20 eq) of tetrabutylammonium hydrogensulfate used as a phase transfer catalyst. The biphasic mixture was jacket cooled to 3° C. and was then mechanically stirred for 3 days. As no further reaction occurred, the reaction mixture was diluted with water and the organic phase was separated. Analysis by thin layer chromatography indicated a 1:1 mixture of the end product and the starting material. The dichloromethane layer was evaporated to a gum. The gum was diluted with dichloromethane and mixed with 1:1 alumina/sand to immobilize it as a solid for Soxhlet extraction. The dichloromethane was evaporated and the solid was put into a Soxhlet extraction thimble and extracted with hexane for 4 hours. Since no further extraction occurred after 4 hours, the hexane solution was evaporated to an oil. The oil was chromatographed over silica gel (EtOAc) and the resultant solid rechromatographed through alumina ($Et_2O$) to yield a solid. The solid was recrystallized from $Et_2O$/hexanes to yield 1.22 g (8%) of product, melting point 86°–88° C.

ANALYSIS: Calculated for $C_{29}H_{28}N_2O$: 82.82% C; 6.71% H; 6.66% N; Found: 82.64% C; 6.72% H; 6.61% N.

EXAMPLE 22

9-(2-Fluorobenzylamino)-1,2,3,4-tetrahydroacridin-1-ol maleate

In 250 ml of dry tetrahydrofuran was dissolved 4.89 g of 3,4-dihydro-9-(2-flurobenzylamino)acridin-1(2H)-one. The mechanically stirred solution was cooled to 0° C. under $N_2$ and 14 ml (1 eq) of 1.1M LiAlH$_4$ in Et$_2$O was added over 0.5 hour. After the addition the reaction was complete based on thin layer chromatography and hence it was quenched by adding 2 ml of saturated NH$_4$Cl solution. The inorganics were filtered off and the tetrahydrofuran solution was evaporated to yield a product. The product was recrystallized from dichloromethane hexanes to yield 3.85 g (78%) of a solid, melting point 140°-142° C. To further purify the product 3.39 g of the product was converted to the maleate salt by combining it with 1.1 eq of maleic acid dissolved in isopropanol. The resulting precipitate was recrystallized from 1:4 MeOH/EtOAc to yield 3.75 g of a solid, melting point 151°-152° C.

ANALYSIS: Calculated for $C_{20}H_{19}FN_2O \cdot C_4H_4O_4$: 65.74% C; 5.29% H; 6.39% N. Found: 66.05%c; 5.48% H; 6.42% N.

EXAMPLE 23

9-Phenethylamino-1,2,3,4-tetrahydroacridin-1-ol maleate

In 75 ml of dry tetrahydrofuran was dissolved 2.45 g of 9-amino-3,4-dihydroacridin-1(2H)-one. The solution was cooled in ice and 7.0 ml (1 eq) of 1.1M LiAlH$_4$ in Et$_2$O was added dropwise. After 0.5 hour the reaction was complete. It was neutralized with 0.5 ml saturated NH$_4$Cl solution and the resulting inorganic salts were filtered off. The filtrate was evaporated to a solid which was recrystallized from dichloromethane/hexanes but not purified. Further attempts to purify by recrystallization failed. It was also observed that drying at 110° C. under vacuum caused yellowing of the product. The maleate salt of the product was formed by adding a solution of 1.1 eq maleic acid in isopropanol to a suspension of the product in isopropanol. A solution formed initially but the salt precipitated out over 0.5 hour at ambient temperatures. The salt was filtered off and recrystallized from 5:1 EtOAc/MeOH and dried at 80° C. in vacuo to yield 1.14 g (32%) of a solid, melting point 169° C.

ANALYSIS: Calculated for $C_{21}H_{22}N_2O \cdot C_4H_4O_4$: 69.11% C; 6.03% H; 6.45% N. Found: 69.03% C; 6.09% H; 6.37% N.

EXAMPLE 24

9-Amino-7-chloro-1,2,3,4-tetrahydroacridin-1-ol maleate

In 50 ml of dry tetrahydrofuran was suspended 4.00 g of 9-amino-7-chloro-3,4-dihydroacridin-1(2H)-one. The mechanically stirred mixture was cooled in ice and 14.73 ml (1 eq) of 1.1M QLiAlH$_4$ in ether was added dropwise. After 0.5 hour the reaction was complete. It was quenched with saturated NH$_4$Cl solution and the salts were extracted into 30% potassium hydroxide. The biphasic mixture was diluted with hexanes and the product was collected by filtration, then washed with water and dried in vacuum to yield 3.00 g (75%) of a solid, melting point 164° C. (with decomposition). This product was analyzed to be a quasihydrate. Drying did not yield the product in an anhydrous form, so the maleate salt was prepared by adding 1.1 eq of maleic acid in isopropanol to a suspension of 2.94 g of the product in isopropanol. Initially a solution formed but within a few minutes the salt precipitated out. It was filtered and rinsed with Et$_2$O to yield 3.90 g (91%) of a solid. This was recrystallized from 1:1 MeOH/EtOAc to yield 2.79 g (65%) of a solid, melting point 200° C. (with decomposition).

ANALYSIS: Calculated for $C_{13}H_{13}ClN_2O \cdot C_4H_4O_4$: 55.96% C; 4.70% H; 7.68% N. Found: 56.29% C; 4.98% H; 7.67% N.

EXAMPLE 25

9-Amino-6-chloro-3,4-dihydroacridin-1(2H)-one

In 200 ml of tetrahydrofuran were combined 5.00 g of 4-chloro-2-(3-oxocyclohexen-1-yl)aminobenzonitrile hydrochloride, 4.88 g (2 eq) milled anhydrous K$_2$CO$_3$, and 0.36 g (0.1 eq) of CuBr (CH$_3$)$_2$S used as a catalyst. The mechanically stirred mixture was refluxed overnight. It was then evaporated to a residue and extracted with several portions of MeOH. The insoluble inorganics were dissolved in water to remove any product not extracted by the MeOH, but none were detected. The MeOH extract was evaporated and the residue was chromatographed on silica gel and then the purified product was recrystallized from EtOAc to yield 2.07 g (47%) of a solid, melting point 285°-287° C.

ANALYSIS: Calculated for $C_{13}H_{11}ClN_2O$: 63.27% C; 4.49% H; 11.35% N. Found: 63.48% C; 4.52% H; 11.52% N.

EXAMPLE 26

9-Amino-6-chloro-1,2,3,4-tetrahydroacridin-1-ol maleate

In 60 ml of dry tetrahydrofuran was suspended 2.79 g of 9-amino-6-chloro-3,4-dihydroacridin-1(2H)-one. The mechanically stirred suspension was cooled to 0° C. and 10.3 ml (1 eq) 1.1M LiAlH$_4$ in ether was added slowly over 5 minutes. The mixture became a solution and after 0.5 hour the reaction was complete based on thin layer chromatography analysis. The reaction was quenched with 200 ml of 30% potassium hydroxide solution added slowly. The two layers were separated and the tetrahydrofuran layer was evaporated to a solid. The solid was suspended in water and a minimal amount of 3N HCl was added to dissolve it. The resultant aqueous solution was washed twice with EtOAc and made slightly basic with 10% NaOH. The resultant precipitate was filtered and air dried to yield 2.76 g (98%) of a solid, melting point 235°-236° C. The solid was suspended in 25 ml of isopropanol and a solution of 1.35 g maleic acid in isopropanol was added thereto. A solution was formed first, but after stirring 0.5 hour the salt precipitated. The mixture was then further cooled in ice and filtered to yield 3.70 g of a solid. This was recrystallized from 1:1 EtOAc/MeOH to yield, after drying at 80° C. under vacuum, 2.41 g (58%) of a solid, melting point 190°-191° C. (with decomposition).

ANALYSIS: Calculated for $C_{13}H_{13}ClN_2O \cdot C_4H_4O_4$: 55.98% C; 4.70% H; 7.68% N. Found: 55.95% C; 4.68% H; 7.88% N.

We claim:

1. A compund having the formula

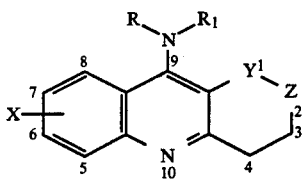

where X is hydrogen, loweralkyl, loweralkoxy, halogen, hydroxy, nitro, NHCOR$_2$ wherein R$_2$ is loweralkyl, or a group of the formula NR$_3$R$_4$ wherein R$_3$ and R$_4$ are independently hydrogen or loweralkyl; R and R$_1$ are independently hydrogen, loweralkyl, phenylloweralkyl, phenylloweralkyl in which the phenyl group is substituted by one or more loweralkyl, loweralkoxy, halogen, hydroxy or trifluoromethyl, diphenylloweralkyl or diphenylloweralkyl in which one or both phenyl groups are substituted by one or more loweralkyl, loweralkoxy, halogen, hydroxy or trifluoromethyl; Y is C=O or CR$_5$OH wherein R$_5$ is hydrogen or loweralkyl; Z is CH$_2$ or C=CR$_6$R$_7$ wherein R$_6$ and R$_7$ are independently hydrogen or loweralkyl; an optical antipode thereof, or a pharmaceutically acceptable acid addition salt thereof.

2. The compound as defined in claim 1, wherein Y is C=O.

3. The compound as defined in claim 2, wherein Z is CH$_2$.

4. The compound as defined in claim 2, wherein Z is C=CR$_6$R$_7$.

5. The compound as defined in claim 4, wherein Z is C=CH$_2$.

6. The compound as defined in claim 3, wherein R is H.

7. The compound as defined in claim 4, wherein R is H.

8. The compound as defined in claim 5, wherein R is H.

9. The compound as defined in claim 6, wherein R$_1$ is H.

10. The compound as defined in claim 7, wherein R$_1$ is H.

11. The compound as defined in claim 8, wherein R$_1$ is H.

12. The compound as defined in claim 6, wherein R$_1$ is loweralkyl.

13. The compound as defined in claim 7, wherein R$_1$ is loweralkyl.

14. The compound as defined in claim 8, wherein R$_1$ is loweralkyl.

15. The compound as defined in claim 6, wherein R$_1$ is phenylloweralkyl.

16. The compound as defined in claim 7, wherein R$_1$ is phenylloweralkyl.

17. The compound as defined in claim 8, wherein R$_1$ is phenylloweralkyl.

18. The compound as defined in claim 6, wherein R$_1$ is halophenylloweralkyl.

19. The compound as defined in claim 7, wherein R$_1$ is halophenylloweralkyl.

20. The compound as defined in claim 8, wherein R$_1$ is halophenylloweralkyl.

21. The compound as defined in claim 6, wherein R$_1$ is diphenylloweralkyl.

22. The compound as defined in claim 7, wherein R$_1$ is diphenylloweralkyl.

23. The compound as defined in claim 8, wherein R$_1$ is diphenylloweralkyl.

24. The compound as defined in claim 3, wherein X is H.

25. The compound as defined in claim 4, wherein X is H.

26. The compound as defined in claim 5, wherein X is H.

27. The compound as defined in claim 6, wherein X is H.

28. The compound as defined in claim 7, wherein X is H.

29. The compound as defined in claim 8, wherein X is H.

30. The compound as defined in claim 9, wherein X is H, which is 9-amino-3,4-dihydroacridin-1(2H)-one.

31. The compound as defined in claim 10, wherein X is H.

32. The compound as defined in claim 11, wherein X is H, which is 9-amino-3,4-dihydro-2-methyleneacridin-1(2H)-one.

33. The compound as defined in claim 12, wherein X is H.

34. The compound as defined in claim 13, wherein X is H.

35. The compound as defined in claim 14, wherein X is H.

36. The compound as defined in claim 15, wherein X is H.

37. The compound as defined in claim 16, wherein X is H.

38. The compound as defined in claim 17, wherein X is H.

39. The compound as defined in claim 18, wherein X is H.

40. The compound as defined in claim 19, wherein X is H.

41. The compound as defined in claim 20, wherein X is H.

42. The compound as defined in claim 21, wherein X is H.

43. The compound as defined in claim 22, wherein X is H.

44. The compound as defined in claim 23, wherein X is H.

45. The compound as defined in claim 6, wherein X is halogen.

46. The compound as defined in claim 7, wherein X is halogen.

47. The compound as defined in claim 8, wherein X is halogen.

48. The compound as defined in claim 6, wherein X is NO$_2$.

49. The compound as defined in claim 7, wherein X is NO$_2$.

50. The compound as defined in claim 8, wherein X is NO$_2$.

51. The compound as defined in claim 6, wherein X is NHCOR$_2$.

52. The compound as defined in claim 7, wherein X is NHCOR$_2$.

53. The compound as defined in claim 8, wherein X is NHCOR$_2$.

54. The compound as defined in claim 6, wherein X is NR$_3$R$_4$.

55. The compound as defined in claim 7, wherein X is NR$_3$R$_4$.

56. The compound as defined in claim 8, wherein X is $NR_3R_4$.

57. The compound as defined in claim 33, wherein $R_1$ is methyl, which is 3,4-dihydro-9-(methylamino)acridin-1(2H)-one.

58. The compound as defined in claim 33, where $R_1$ is n-propyl, which is 3,4-dihydro-9-(n-propylamino)acridin-1(2H)-one.

59. The compound as defined in claim 36, where $R_1$ is benzyl, which is 9-benzylamino-3,4-dihydroacridin-1(2H)-one.

60. The compound as defined in claim 36, where $R_1$ is phenethyl, which is 3,4-dihydro-9-(phenethylamino)acridin-1-2H-one.

61. The compound as defined in claim 39, where $R_1$ is 2-fluorobenzyl, which is 3,4-dihydro-9-(2-fluorobenzylamino)acridin-1(2H)-one.

62. The compound as defined in claim 42, where $R_1$ is 4,4-diphenylbutyl, which is 3,4-dihydro-9-(4,4-diphenylbutylamino)acridin-1(2H)-one.

63. The compound as defined in claim 45, where $R_1$ is H.

64. The compound as defined in claim 63, where X is chlorine.

65. The compound as defined in claim 64, where X is 7-chloro, which is 9-amino-7-chloro-3,4-dihydroacridin-1(2H)-one.

66. The compound as defined in claim 64, where X is 6-chloro, which is 9-amino-6-chloro-3,4-dihydroacridin-1(2H)-one.

67. The compound as defined in claim 48, where $R_1$ is H.

68. The compound as defined in claim 67, where X is 7-$NO_2$, which is 9-amino-3,4-dihydro-7-nitroacridin-1(2H)-one.

69. The compound as defined in claim 48, where $R_1$ is methyl.

70. The compound as defined in claim 69, where X is 7-$NO_2$, which is 3,4-dihydro-9-methylamino-7-nitroacridin-1(2H)-one.

71. The compound as defined in claim 51, where $R_1$ is H.

72. The compound as defined in claim 71, where X is $NHCOCH_3$.

73. The compound as defined in claim 72, where X is 7-$NHCOCH_3$, which is N-[9-amino-3,4-dihydro-1(2H)-oxoacridin-7-yl]-acetamide.

74. The compound as defined in claim 54, where $R_1$ is H.

75. The compound as defined in claim 74, where X is $NH_2$.

76. The compound as defined in claim 75, where X is 7-$NH_2$, which is 7,9-diamino-3,4-dihydroacridin-1(2H)-one.

77. The compound as defined in claim 1, wherein Y is $CR_5OH$.

78. The compound as defined in claim 77, wherein $R_5$ is H.

79. The compound as defined in claim 78, wherein Z is $CH_2$.

80. The compound as defined in claim 78, wherein Z is $C=CR_6R_7$.

81. The compound as defined in claim 80, wherein Z is $C=CH_2$.

82. The compound as defined in claim 79, wherein R is H.

83. The compound as defined in claim 80, wherein R is H.

84. The compound as defined in claim 81, wherein R is H.

85. The compound as defined in claim 82, wherein $R_1$ is H.

86. The compound as defined in claim 83, wherein $R_1$ is H.

87. The compound as defined in claim 84, wherein $R_1$ is H.

88. The compound as defined in claim 82, wherein $R_1$ is loweralkyl.

89. The compound as defined in claim 83, wherein $R_1$ is loweralkyl.

90. The compound as defined in claim 84, wherein $R_1$ is loweralkyl.

91. The compound as defined in claim 82, wherein $R_1$ is phenylloweralkyl.

92. The compound as defined in claim 83, wherein $R_1$ is phenylloweralkyl.

93. The compound as defined in claim 84, wherein $R_1$ is phenylloweralkyl.

94. The compound as defined in claim 82, wherein $R_1$ is halophenylloweralkyl.

95. The compound as defined in claim 83, wherein $R_1$ is halophenylloweralkyl.

96. The compound as defined in claim 84, wherein $R_1$ is halophenylloweralkyl.

97. The compound as defined in claim 79, wherein X is H.

98. The compound as defined in claim 80, wherein X is H.

99. The compound as defined in claim 81, wherein X is H.

100. The compound as defined in claim 82, wherein X is H.

101. The compound as defined in claim 83, wherein X is H.

102. The compound as defined in claim 84, wherein X is H.

103. The compound as defined in claim 85, wherein X is H, which is 9-amino-1,2,3,4-tetrahydroacridin-1-ol.

104. The compound as defined in claim 86, wherein X is H.

105. The compound as defined in claim 87, wherein X is H.

106. The compound as defined in claim 88, wherein X is H.

107. The compound as defined in claim 89, wherein X is H.

108. The compound as defined in claim 90, wherein X is H.

109. The compound as defined in claim 91, wherein X is H.

110. The compound as defined in claim 92, wherein X is H.

111. The compound as defined in claim 93, wherein X is H.

112. The compound as defined in claim 94, wherein X is H.

113. The compound as defined in claim 95, wherein X is H.

114. The compound as defined in claim 96, wherein X is H.

115. The compound as defined in claim 82, wherein X is halogen.

116. The compound as defined in claim 83, wherein X is halogen.

117. The compound as defined in claim 84, wherein X is halogen.

118. The compound as defined in claim 106, wherein R₁ is methyl, which is 9-methylamino-1,2,3,4-tetrahydroacridin-1-ol.

119. The compound as defined in claim 106, wherein R₁ is n-propyl, which is 9-(n-propylamino)-1,2,3,4-tetrahydroacridin-1-ol.

120. The compound as defined in claim 109, wherein R₁ is benzyl, which is 9-benzylamino-1,2,3,4-tetrahydroacridin-1-ol.

121. The compound as defined in claim 109, wherein R₁ is phenethyl, which is 9-phenethylamino-1,2,3,4-tetrahydroacridin-1-ol.

122. The compound as defined in claim 112, wherein R₁ is 2-fluorobenzyl, which is 9-(2-fluorobenzylamino)-1,2,3,4-tetrahydroacridin-1-ol.

123. The compound as defined in claim 115, where R₁ is H.

124. The compound as defined in claim 123, where X is chlorine.

125. The compound as defined in claim 124, where X is 7-chloro, which is 9-amino-7-chloro-1,2,3,4-tetrahydroacridin-1-ol.

126. The compound as defined in claim 124, where X is 6-chloro, which is 9-amino-6-chloro-1,2,3,4-tetrahydroacridin-1-ol.

127. The compound as defined in claim 77, wherein R₅ is loweralkyl.

128. The compound as defined in claim 127, where R₅ is methyl.

129. The compound as defined in claim 128, where R is H.

130. The compound as defined in claim 129, where R₁ is H.

131. The compound as defined in claim 130, where X is H, which is 9-amino-1-methyl-1,2,3,4-tetrahydroacridin-1-ol.

132. A pharmaceutical composition which comprises an effective memory enhancing amount of a compound defined in claim 1.

133. A pharmaceutical composition which comprises an effective memory enhancing amount of a compound defined in claim 3.

134. A pharmaceutical composition which comprises an effective memory enhancing amount of a compound defined in claim 79.

135. A pharmaceutical composition which comprises an effective memory enhancing amount of a compound defined in claim 91.

136. A pharmaceutical composition which comprises an effective memory enhancing amount of a compound defined in claim 103.

137. A pharmaceutical composition which comprises an effective memory enhancing amount of a compound defined in claim 120.

138. A method of treating a patient in need of memory enhancement, wherein an effective memory enhancing amount of a compound defined in claim 1 is administered to the patient.

139. A method of treating a patient in need of memory enhancement, wherein an effective memory enhancing amount of a compound defined in claim 3 is administered to the patient.

140. A method of treating a patient in need of memory enhancement, wherein an effective memory enhancing amount of a compound defined in claim 79 is administered to the patient.

141. A method of treating a patient in need of memory enhancement, wherein an effective memory enhancing amount of a compound defined in claim 91 is administered to the patient.

142. A method of treating a patient in need of memory enhancement, wherein an effective memory enhancing amount of a compound defined in claim 103 is administered to the patient.

143. A method of treating a patient in need of memory enhancement, wherein an effective memory enhancing amount of a compound defined in claim 120 is administered to the patient.

* * * * *